US009115306B2

(12) United States Patent
Cranor et al.

(10) Patent No.: US 9,115,306 B2
(45) Date of Patent: Aug. 25, 2015

(54) LOW TEMPERATURE OXALATE SYSTEMS AND METHODS FOR CHEMILUMINESCENT REACTIONS

(71) Applicant: Cyalume Technologies, West Springfield, MA (US)

(72) Inventors: Earl Cranor, Longmeadow, MA (US); Linda Jacob, Woodbridge, CT (US); Patrick Taylor, Holyoke, MA (US)

(73) Assignee: Cyalume Technologies, Inc., West Springfield, MA (US)

( * ) Notice: Subject to any disclaimer, the term of this patent is extended or adjusted under 35 U.S.C. 154(b) by 0 days.

(21) Appl. No.: 14/294,058

(22) Filed: Jun. 2, 2014

(65) Prior Publication Data
US 2014/0353560 A1 Dec. 4, 2014

Related U.S. Application Data

(60) Provisional application No. 61/830,075, filed on Jun. 1, 2013, provisional application No. 61/830,071, filed on Jun. 1, 2013, provisional application No. 61/830,072, filed on Jun. 1, 2013, provisional application No. 61/830,070, filed on Jun. 1, 2013.

(51) Int. Cl.
C09K 11/07 (2006.01)
C09K 11/02 (2006.01)
G01N 21/76 (2006.01)

(52) U.S. Cl.
CPC ............... *C09K 11/07* (2013.01); *C09K 11/025* (2013.01); *G01N 21/76* (2013.01); *C09K 2211/1007* (2013.01); *C09K 2211/1018* (2013.01)

(58) Field of Classification Search
USPC ............................................. 252/700; 362/34
See application file for complete search history.

(56) References Cited

U.S. PATENT DOCUMENTS

| 2012/0097063 A1* | 4/2012 | Cranor et al. ............. 102/513 |
| 2012/0126188 A1 | 5/2012 | Schrimmer |
| 2014/0353558 A1 | 12/2014 | Cranor et al. |
| 2014/0353559 A1 | 12/2014 | Cranor et al. |
| 2014/0356975 A1 | 12/2014 | Cranor et al. |

OTHER PUBLICATIONS

International Search Report and Written Opinion from International Application No. PCT/US2014/040573 dated Oct. 15, 2014.

* cited by examiner

*Primary Examiner* — Vu A Nguyen
(74) *Attorney, Agent, or Firm* — Greenberg Traurig, LLP

(57) ABSTRACT

In some embodiments, the instant invention provides a chemiluminescent system, including: an oxalate system, including: (a) at least one oxalate ester in an amount ranging from 3 to 60 percent by weight based on a total weight of the oxalate system, (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, in an amount ranging from 10 to 97 percent by weight based on the total weight of the oxalate system, (c) at least one second solvent is selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, (d) at least one fluorescer, and (e) at least one inorganic salt in an amount ranging from 0.1 to 30 percent by weight based on the total weight of the oxalate system.

6 Claims, 2 Drawing Sheets

LOW TEMPERATURE OXALATE SYSTEMS AND METHODS FOR CHEMILUMINESCENT REACTIONS

RELATED APPLICATIONS

This application claims the priority of U.S. provisional application Ser. No. 61/830,070, filed Jun. 1, 2013, entitled "BROAD TEMPERATURE PERFORMANCE CHEMILUMINESCENT SYSTEMS AND METHODS", Ser. No. 61/830,071, filed Jun. 1, 2013, entitled "LOW TEMPERATURE OXALATE SYSTEMS AND METHODS FOR CHEMILUMINESCENT REACTIONS", Ser. No. 61/830,072, filed Jun. 1, 2013, entitled "LOW TEMPERATURE ACTIVATOR SYSTEMS AND METHODS FOR CHEMILUMINESCENT REACTIONS", and Ser. No. 61/830,075, filed Jun. 1, 2013, entitled "MIXED CATALYST SYSTEMS AND METHODS FOR CHEMILUMINESCENT REACTIONS," which are incorporated herein by reference in their entireties for all purposes.

TECHNICAL FIELD

In some embodiments, the present invention relates to chemiluminescent systems and methods.

BACKGROUND

Chemiluminescence is the emission of light as a result of a chemical reaction. There may also be limited emission of heat during the chemical reaction. Typically, a reaction beginning with reactants A and B, with an excited intermediate, yields products and light. Typically, there are many applications that use chemiluminescence. For example, chemiluminescence is used in gas analysis, analysis of inorganic and/or organic species, detection and assay of biomolecules, DNA sequencing, lighting objects, and children's toys.

BRIEF SUMMARY OF INVENTION

In some embodiments, the instant invention provides a chemiluminescent system, including: an oxalate system, including: (a) at least one oxalate ester in an amount ranging from 3 to 60 percent by weight based on a total weight of the oxalate system, (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, and a combination thereof; where the at least one first solvent is present in an amount ranging from 10 to 97 percent by weight based on the total weight of the oxalate system, (c) at least one second solvent is selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, and a combination thereof; where the at least one second solvent is present in an amount ranging from 10 to 97 percent by weight based on the total weight of the oxalate system, (d) at least one fluorescer, and (e) at least one inorganic salt in an amount ranging from 0.1 to 30 percent by weight based on the total weight of the oxalate system, where a viscosity of the chemiluminescent system does not exceed 130,000 cP; and where a combination of the at least one first solvent and the at least one second solvent is present in a sufficient amount in the chemiluminescent system so as to result the chemiluminescent system, at a temperature ranging from −110 degrees Celsius to −10 degrees Celsius, producing a light having an illuminescence between 0.1 lx and 35,000 lx.

In some embodiments, the at least one oxalate ester is represented by formula (I):

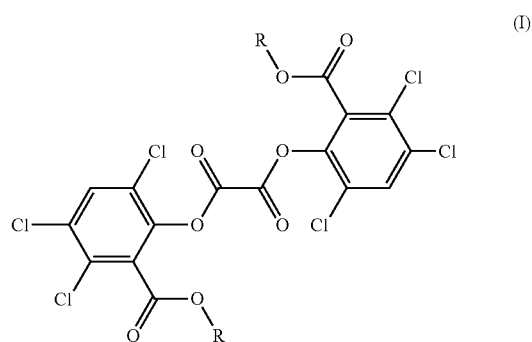

where R=CH$_2$A, and A is selected from the group consisting of an alkyl chain, alkyl ring, an aromatic ring, and a combination thereof, where R is linear or branched, and where R is from C4-15.

In some embodiments, the at least one oxalate ester is selected from the group consisting of: bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(3-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-trichloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,46-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)ethoxy]

carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

In some embodiments, the at least one fluorescer is selected from the group consisting of: 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene, 2-chloro-9,10-bis(4-methoxyphenyl)anthracene, 9,10-bis(phenylethynyl)anthracene, 1-chloro-9,10-bis(phenylethynyl)anthracene, 1,8-dichloro-9,10-bis(phenylethynyl)anthracene, 1,5-dichloro-9,10-bis(phenylethynyl)anthracene, 2,3-dichloro-9,10-bis(phenylethynyl)anthracene, 5,12-bis(phenylethynyl)tetracene, 9,10-diphenylanthracene, 1,6,7,12-tetraphenoxy-N,N'-bis(2,6-diisopropylphenyl)-3,4,9,10-perylene dicarboximide, 1,6,7,12-tetraphenoxy-N,N' bis(2,5-di-t-butylphenyl)-3,4,9,10-perylene dicarboximide, 1,7-dichloro-6,12-diphenoxy-N,N'-bis(2,6-diisopropylphenyl)-3,4,9,10-perylenedicarboximide, 1,6,7,12-tetra(p-bromophenoxy)-N,N'-bis(2,6-diisopropylphenyl)-3,4,9,10-perylene dicarboximide, 1,6,7,12-tetraphenoxy-N,N' dineopentyl-3,4,9,10-perylene dicarboximide, 1,6,7,12-tetra-(p-t-butylphenoxy)-N,N'-dineopentyl-3,4,9,10-perylenedicarboximide, 1,6,7,12-tetra(o-chlorophenoxy)-N,N'-bis(2,6-diisopropylphenyl)-3,4,9,10-perylenedicarboximide; 1,6,7,12-tetra(p-chlorophenoxy)-N,N'-bis(2,6-diisopropylphenyl)-3,4,9,10-perylene dicarboximide, 1,6,7,12-tetra(o-fluorophenoxy)-N,N'-bis(2,6-diisopropylphenyl)-3,4,9,10-perylene dicarboximide, 1,6,7,12-tetra(p-fluorophenoxy)-N,N'-bis(2,6-diisopropylphenyl)-3,4,9,10-perylenedicarboximide, 1,6,7,12-tetraphenoxy-N,N'-diethyl-3,4,9,10-perylene dicarboximide, 1,7-dibromo-6,12-diphenoxy-N,N'-bis(2-isopropylphenyl)-3,4,9,10-perylene dicarboximide, 16,17-dihexyloxyviolanthrone, and 1,4-dimethyl-9,10-bis(phenylethynyl)anthracene.

In some embodiments, the at least one inorganic salt is selected from the group consisting of: sodium thiosulphate, potassium thiosulphate, cobalt acetate, copper acetate, lead acetate, cupric chloride, ferric chloride, calcium iodide, potassium iodide, and silver nitrate.

In some embodiments, the at least one fluorescer is present in an amount ranging from 0.05 to 0.9 percent by weight based on the total weight of the oxalate system.

BRIEF DESCRIPTION OF THE DRAWINGS

The present invention will be further explained with reference to the attached figures. The figures constitute a part of this specification and include illustrative embodiments of the present invention and illustrate various objects and features thereof. The figures shown are not necessarily to scale, with emphasis instead generally being placed upon illustrating the principles of the present invention. Further, some features may be exaggerated to show details of particular components.

Figure 1:
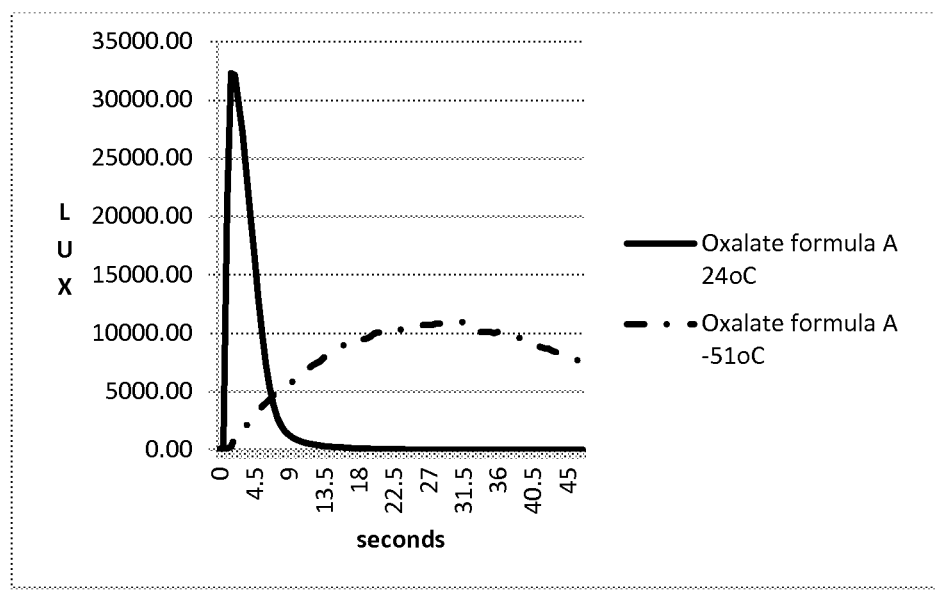
FIG. 1 illustrates aspects of some embodiments of the instant invention.

Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

"Activation" and variations thereof, as used herein, means that the oxalate system of the present invention and an activator system containing peroxide and at least one catalyst have been sufficiently combined such as by mixing to provide useable light useable light in a short period such as less than a minute at low temperatures such as down –110 degrees C. In some embodiments, the oxalate system of the present disclosure produces useable light at low temperatures when activated.

In some embodiments, the present invention relates to an oxalate system for a chemiluminescent reaction for production of useable light in a short period such as less than a minute at low temperatures down to –110 degrees C. In some embodiments, the oxalate system can be used in military and non-military training, emergency, and situations where potential ignition sources are hazardous when combined with a suitable activator system.

Tracers are employed that allow an observer to visually trace a projectile's trajectory, such as after the firing of munitions in training or combat situations. Winter and high altitude conditions can greatly diminish the effectiveness of current chemiluminescent markers.

In some embodiments, the present invention is an oxalate system that includes least one oxalate ester, at least one dye, at least one first solvent, and at least one inorganic salt, wherein, when the oxalate system is combined with an activator system to form a chemiluminescent system, the chemiluminescent system is configured to produces light to a temperature of −110 degrees C.

In some embodiments, the at least one oxalate ester is selected from the group consisting of bis(2,4,5-trichloro-6-carbopentoxyphenyl)oxalate; bis(2,4,5-trichlorophenyl)oxalate; bis(2,4,5-tribromo-6-carbohexoxyphenyl)oxalate; bis(2,4,5-trichloro-6-carboisopentoxyphenyl)oxalate; bis(2,4,5-trichloro-6-carbobenzoxyphenyl)oxalate; bis(2-nitrophenyl)oxalate; bis(2,4-dinitrophenyl)oxalate; bis(2,6-dichloro-4-nitrophenyl)oxalate; bis(2,4,6-trichlorophenyl)oxalate; bis(3-trifluoromethyl-4-nitrophenyl)oxalate; bis(2-methyl-4,6-dinitrophenyl)oxalate; bis(1,2-dimethyl-4,6-dinitrophenyl)oxalate; bis(2,4-dichlorophenyl)oxalate; bis(2,4-dinitrophenyl)oxalate; bis(2,5-dinitrophenyl)oxalate; bis(2-formyl-4-nitrophenyl)oxalate; bis(pentachlorophenyl)oxalate; bis(1,2-dihydro-2-oxo-1-pyridyl)glyoxal; bis(2,4-dinitro-6-methylphenyl)oxalate; and bis-N-phthalimidyl oxalate.

In some embodiments, the at least one oxalate ester is selected from the group of oxalate esters represented by the general formula (I)

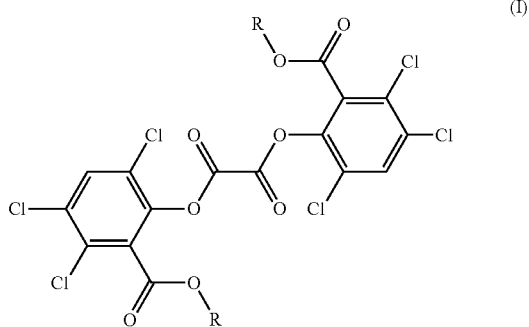

(I)

wherein R=CH$_2$A, and A is chosen from alkyl chains, alkyl rings, and aromatic rings or combinations thereof, and wherein R is linear or nonlinear, and comprises from 4-15 carbon atoms.

In some embodiments, the at least one oxalate ester is selected from the group consisting of bis{3,4,6-trichloro-2-[(2-methylpropoxy)carbonyl]phenyl}oxalate; bis{3,4,6-trichloro-2-[(cyclopropylmethoxy)carbonyl]phenyl}oxalate; bis{3,4,6-trichloro-2-[(2-methylbutoxy)carbonyl]phenyl}oxalate; bis{3,4,6-trichloro-2-[(3-methylbutoxy)carbonyl]phenyl}oxalate; bis{3,4,6-trichloro-2-[(2,2-dimethylpropoxy)carbonyl]phenyl}oxalate; bis{3,4,6-trichloro-2-[(2-methylpentyloxy)carbonyl]phenyl}oxalate; bis{3,4,6-trichloro-2-[(3-methylpentyloxy)carbonyl]phenyl}oxalate; bis{3,4,6-trichloro-2-[(4-methylpentyloxy)carbonyl]phenyl}oxalate; bis{3,4,6-trichloro-2-[(3,3-dimethylbutoxy)carbonyl]phenyl}oxalate; bis{3,4,6-trichloro-2-[(2-ethylbutoxy)carbonyl]phenyl}oxalate; bis{3,4,6-trichloro-2-[(cyclopentylmethoxy)carbonyl]phenyl}oxalate; bis{3,4,6-trichloro-2-[(2-methylhexyloxy)carbonyl]phenyl}oxalate; bis{3,4,6-trichloro-2-[(3-methylhexyloxy)carbonyl]phenyl}oxalate; bis{3,4,6-trichloro-2-[(4-methylhexyloxy)carbonyl]phenyl}oxalate; bis{3,4,6-trichloro-2-[(5-methylhexyloxy)carbonyl]phenyl}oxalate; bis{3,4,6-trichloro-2-[(cyclohexylmethoxy)carbonyl]phenyl}oxalate; bis{3,4,6-trichloro-2-[(phenylmethoxy)carbonyl]phenyl}oxalate; bis{3,4,6-trichloro-2-[(2-phenylethoxy)carbonyl]phenyl}oxalate; bis (3,4,6-trichloro-2-{[(2-methylphenyl)methoxy]carbonyl}phenyl)oxalate; bis(3,4,6-trichloro-2-{[(3-methylphenyl)methoxy]carbonyl}phenyl)oxalate; bis(3,4,6-trichloro-2-{[(4-methylphenyl)methoxy]carbonyl}phenyl)oxalate; bis(3,4,6-trichloro-2-{[(2,3-dimethylphenyl)methoxy]carbonyl}phenyl)oxalate; bis(3,4,6-trichloro-2-{[(2,4-dimethylphenyl)methoxy]carbonyl}phenyl)oxalate; bis(3,4,6-trichloro-2-{[3,4-dimethylphenyl)methoxy]carbonyl}phenyl)oxalate; bis(3,4,6-trichloro-2-{[(3,5-dimethylphenyl)methoxy]carbonyl}phenyl)oxalate; bis(3,4,6-trichloro-2-{[(2,6-dimethylphenyl)methoxy]carbonyl}phenyl)oxalate; bis(3,4,6-trichloro-2-{[(2-ethylphenyl)methoxy]carbonyl)phenyl)oxalate; bis(3,4,6-trichloro-2-{[(3-ethylphenyl)methoxy]carbonyl}phenyl)oxalate; bis(3,4,6-trichloro-2-{[(4-ethylphenyl)methoxy]carbonyl}phenyl)oxalate; bis(3,4,6-trichloro-2-{[2-(2-methylphenyl)ethoxy]carbonyl}phenyl)oxalate; bis(3,4,6-trichloro-2-{[2-(3-methylphenyl)ethoxy]carbonyl}phenyl)oxalate; bis(3,4,6-trichloro-2-{[2-(4-methylphenyl)ethoxy]carbonyl}phenyl)oxalate; bis{3,4,6-trichloro-2-[(2-phenylpropoxy)carbonyl]phenyl}oxalate; bis(3,4,6-trichloro-2-[(3-phenylpropoxy)carbonyl]phenyl}oxalate; bis{3,4,6-trichloro-2[1-naphthalenylmethoxy)carbonyl]phenyl}oxalate; bis{3,4,6-trichloro-2-[2-naphthalenyl-methoxy)carbonyl]phenyl}oxalate; bis{3,4,6-trichloro-2-[(2,2-diphenylethoxy)carbonyl]phenyl}oxalate; bis{3,4,6-trichloro-2-[(9-fluorenylmethoxy)carbonyl]phenyl}oxalate; and bis{3,4,6-trichloro-2-[(9-anthracenylmethoxy)carbonyl]phenyl}oxalate.

In some embodiments, the at least one oxalate ester is present in an amount ranging from 3 percent to 60 percent by weight, based on the total weight of the oxalate system.

In some embodiments, the at least one first solvent is selected from the group consisting of alkyl benzoates, dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, acetyl trialkyl citrates, 2-acetyloxy isobutyrates, paraffinic liquids, isoparaffinic liquids, toluene, an nitroethane.

In some embodiments, the at least one dye is a fluorescer selected from the group consisting of 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene; 2-chloro-9,10-bis(4-methoxyphenyl)anthracene; 9,10-bis(phenylethynyl)anthracene; 1-chloro-9,10-bis(phenylethynyl)anthracene; 1,8-dichloro-9,10-bis(phenylethynyl)anthracene; 1,5-dichloro-9,10-bis(phenylethynyl)anthracene; 2,3-dichloro-9,10-bis(phenylethynyl)anthracene; 5,12-bis(phenylethynyl)tetracene, 9,10-diphenylanthracene; 1,6,7,12-tetraphenoxy-N,N'-bis(2,6-diisopropylpheny l)-3,4,9,10-perylene dicarboximide; 1,6,7,12-tetraphenoxy-N,N' bis (2,5-di-t-butylphenyl)-3,4,9,10-perylene dicarboximide; 1,7-dichloro-6,12-diphenoxy-N,N'-bis(2,6-diisopropylphenyl)-3,4,9,10-perylene dicarboximide; 1,6,7,12-tetra(p-bromophenoxy)-N,N'-bis(2,6-diisopropylphenyl)-3,4,9,10-perylene dicarboximide; 1,6,7,12-tetraphenoxy-N,N' dineopentyl-3,4,9,10-perylene dicarboximide; 1,6,7,12-tetra-(p-t-butylphenoxy)-N,N'-dineopentyl-3,4,9,10-perylenedicarboximide; 1,6,7,12-tetra(o-chlorophenoxy)-N,N'-bis(2,6-diisopropylphenyl)-3,4,9,10-perylenedicarboximide; 1,6,7,12-tetra(p-chlorophenoxy)-N,N'-bis(2,6-diisopropylphenyl)-3,4,9,10-perylene dicarboximide; 1,6,7,12-tetra(o-fluorophenoxy)-N,N'-bis(2,6-diisopropylphenyl)-3,4,9,10-perylene dicarboximide; 1,6,7,12-tetra(p-fluorophenoxy)-N,N'-bis(2,6-diisopropylphenyl)-3,4,9,10-perylenedicarboximide; 1,6,7,12- tetraphenoxy-N,N'-diethyl-3,4,9,10-perylene dicarboximide; 1,7-dibromo-6,12-diphenoxy-N,N'-bis(2-isopropylphenyl)-3,4,9,10-perylene dicarboximide; 16,17-dihexyloxyviolanthrone; and 1,4-dimethyl-9,10-bis(phenylethynyl)anthracene.

In some embodiments, the at least one dye is a fluorescer present in an amount ranging from 0.05 percent to 0.9 percent by weight, based on the total weight of the oxalate system.

In some embodiments, the at least one inorganic salt is selected from the group consisting of sodium thiosulphate, potassium thiosulphate, cobalt acetate, copper acetate, lead acetate, cupric chloride, ferric chloride, calcium iodide, potassium iodide, and silver nitrate.

In some embodiments, the at least one inorganic salt is present in an amount ranging from 0.1 percent to 30 percent by weight, based on the total weight of the oxalate system.

In some embodiments, the activator system may include at least one peroxide that may include, but is not limited to, hydrogen peroxide; sodium peroxide; sodium perborate; sodium pyrophosphate peroxide; urea peroxide; histidine peroxide; t-butylhydroperoxide; peroxybenzoic acid, and sodium percarbonate; at least one catalyst that may include, but is not limited to, alkali benzoates, alkali salicylates, alkali anisates, tertiary amines, or nitrogenous heterocyclic aliphatic and aromatic compounds; at least one bridging solvent if necessary to ensure solubility of the peroxide in the activator composition that may include, but is not limited to tertiary alcohols, glycols and their mono or di ethers, esters of 2-hydroxyisobutyrates; and low melting point solvents that may include, but are not limited to, trialkyl citrates, dialkyl phthalates, glycols, and glycol ethers or any combination thereof.

In some embodiments, the ratio of the weight of the oxalate system to the weight of the activator system ranges from 1:9 to 4:1. In some embodiments, the ratio of the weight of the oxalate system to the weight of the activator system ranges from 1:5 to 2:1. In some embodiments, the ratio of the weight of the oxalate system to the weight of the activator system ranges from 1:1 to 3:1. In some embodiments, the ratio of the weight of the oxalate system to the weight of the activator system ranges from 1:3 to 3:1. In some embodiments, the ratio of the weight of the oxalate system to the weight of the activator system ranges from 1:2 to 2:1. In some embodiments, the ratio of the weight of the oxalate system to the weight of the activator system ranges from 2:1 to 4:1. In some embodiments, the ratio of the weight of the oxalate system to the weight of the activator system ranges from 1:6 to 2:1. In some embodiments, the ratio of the weight of the oxalate system to the weight of the activator system ranges from 1:1 to 4:1.

In some embodiments, the ratio of the weight of the oxalate system to the weight of the activator system is 1:9. In some embodiments, the ratio of the weight of the oxalate system to the weight of the activator system is 1:2. In some embodiments, the ratio of the weight of the oxalate system to the weight of the activator system is 2:1. In some embodiments, the ratio of the weight of the oxalate system to the weight of the activator system is 3:1. In some embodiments, the ratio of the weight of the oxalate system to the weight of the activator system is 1:8. In some embodiments, the ratio of the weight of the oxalate system to the weight of the activator system is 4:1. In some embodiments, the ratio of the weight of the oxalate system to the weight of the activator system is 8:2. In some embodiments, the ratio of the weight of the oxalate system to the weight of the activator system is 1:5. In some embodiments, the ratio of the weight of the oxalate system to the weight of the activator system is 1:3.

In some embodiments, the system of the present invention, when activated, is configured to produce useable light in a temperature range of −110° C. to 75° C. In some embodiments, the system of the present invention, when activated, is configured to produce useable light in a temperature range of −80° C. to 50° C. In some embodiments, the system of the present invention, when activated, is configured to produce useable light in a temperature range of −110° C. to 50° C. In some embodiments, the system of the present invention, when activated, is configured to produce useable light in a temperature range of −80° C. to 75° C. In some embodiments, the system of the present invention, when activated, is configured to produce useable light in a temperature range of −30° C. to 30° C. In some embodiments, the system of the present invention, when activated, is configured to produce useable light in a temperature range of −100° C. to 0° C. In some embodiments, the system of the present invention, when activated, is configured to produce useable light in a temperature range of −20° C. to 75° C. In some embodiments, the system of the present invention, when activated, is configured to produce useable light in a temperature down to −110° C. In some embodiments, the system of the present invention, when activated, is configured to produce useable light in a temperature range of −60° C. to 20° C. In some embodiments, the system of the present invention, when activated, is configured to produce useable light in a temperature range of −110° C. to −10° C.

In some embodiments, the system of the present invention, when activated, is configured to produce useable light for a duration of 1 second to 3 minutes. In some embodiments, the system of the present invention, when activated, is configured to produce useable light for a duration of 10 second to 3 minutes. In some embodiments, the system of the present invention, when activated, is configured to produce useable light for a duration of 1 second to 2 minutes. In some embodiments, the system of the present invention, when activated, is configured to produce useable light for a duration of 30 second to 1 minute. In some embodiments, the system of the present invention, when activated, is configured to produce useable light for a duration of 20 second to 2 minute. In some embodiments, the system of the present invention, when activated, is configured to produce useable light for a duration of 2 minutes to 3 minute. In some embodiments, the system of the present invention, when activated, is configured to produce useable light for a duration of 1 minute to 2 minutes.

In some embodiments, the system of the present invention, when activated, is configured to produce useable light for a duration of 10 seconds. In some embodiments, the system of the present invention, when activated, is configured to produce useable light for a duration of 1 minute. In some embodiments, the system of the present invention, when activated, is configured to produce useable light for a duration of 30 seconds. In some embodiments, the system of the present invention, when activated, is configured to produce useable light for a duration of 2 minutes. In some embodiments, the system of the present invention, when activated, is configured to produce useable light for a duration of 15 seconds. In some embodiments, the system of the present invention, when activated, is configured to produce useable light for a duration of 1.5 minute. In some embodiments, the system of the present invention, when activated, is configured to produce useable light for a duration of 45 seconds.

In some embodiments, the oxalate system is comprised of at least one oxalate ester, at least one dye or fluorescer, at least one inorganic salt, and at least one solvent that may include a sufficiently low melting point and compatibility with the chemical reactions needed to produce chemiluminescence.

In some embodiments, the at least one oxalate ester useful in the present disclosure include but are not limited to bis(2,4,5-trichloro-6-carbopentoxyphenyl)oxalate (CPPO); bis(2,4,5-trichlorophenyl)oxalate; bis(2,4,5-tribromo-6-carbohexoxyphenyl)oxalate; bis(2,4,5-trichloro-6-carboisopentoxyphenyl)oxalate; bis(2,4,5-trichloro-6-carbobenzoxyphenyl) oxalate; bis(2-nitrophenyl)oxalate; bis (2,4-dinitrophenyl)oxalate; bis(2,6-dichloro-4-nitrophenyl)oxalate; bis(2,4,6-trichlorophenyl)oxalate; bis(3-trifluoromethyl-4-nitrophenyl)oxalate; bis(2-methyl-4,6-dinitrophenyl)oxalate; bis(1,2-dimethyl-4,6-dinitrophenyl)oxalate; bis(2,4-dichlorophenyl)oxalate; bis(2,4-dinitrophenyl)oxalate; bis(2,5-dinitrophenyl)oxalate; bis(2-formyl-4-nitrophenyl)oxalate; bis(pentachlorophenyl)-oxalate; bis(1,2-dihydro-2-oxo-1-pyridyl)glyoxal; bis(2,4-dinitro-6-methylphenyl)oxalate; bis-N-phthalimidyl oxalate.

In some embodiments, the at least one oxalate ester is represented by the general formula (1),

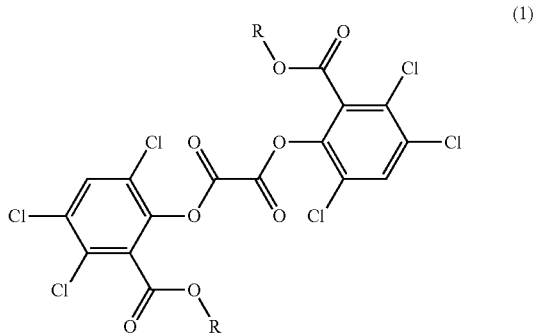

(1)

wherein R=CH$_2$A and A is chosen from alkyl chains, alkyl rings, and aromatic rings or combinations thereof, such that R is linear or nonlinear, and further such that R comprises from 4-15 carbons, as well as mixtures of any of the foregoing oxalates.

In some embodiments, the at least one oxalate ester is from a group that includes but is not limited to: bis{3,4,6-trichloro-2-[(2-methylpropoxy)carbonyl]phenyl}oxalate; bis{3,4,6-trichloro-2-[(cyclopropylmethoxy)carbonyl]phenyl}oxalate; bis{3,4,6-trichloro-2-[(2-methylbutoxy)carbonyl]phenyl}oxalate; bis{3,4,6-trichloro-2-[(3-methylbutoxy)carbonyl]phenyl}oxalate; bis{3,4,6-trichloro-2-[(2,2-dimethylpropoxy)carbonyl]phenyl}oxalate; bis{3,4,6-trichloro-2-[(2-methylpentyloxy)carbonyl]phenyl}oxalate; bis{3,4,6-trichloro-2-[(3-methylpentyloxy)carbonyl]phenyl}oxalate; bis{3,4,6-trichloro-2-[(4-methylpentyloxy)carbonyl]phenyl}oxalate; bis{3,4,6-trichloro-2-[(3,3-dimethylbutoxy)carbonyl]phenyl}oxalate; bis{3,4,6-trichloro-2-[(2-ethylbutoxy)carbonyl]phenyl}oxalate; bis{3,4,6-trichloro-2-[(cyclopentylmethoxy)carbonyl]phenyl}oxalate; bis{3,4,6-trichloro-2-[(2-methylhexyloxy)carbonyl]phenyl}oxalate; bis{3,4,6-trichloro-2-[(3-methylhexyloxy)carbonyl]phenyl}oxalate; bis{3,4,6-trichloro-2-[(4-methylhexyloxy)carbonyl]phenyl}oxalate; bis{3,4,6-trichloro-2-[(5-methylhexyloxy)carbonyl]phenyl}oxalate; bis{3,4,6-trichloro-2-[(cyclohexylmethoxy)carbonyl]phenyl}oxalate; bis{3,46-trichloro-2-[(phenylmethoxy)carbonyl]phenyl}oxalate; bis{3,4,6-trichloro-2-[(2-phenylethoxy)carbonyl]phenyl}oxalate; bis (3,4,6-trichloro-2-{[(2-methylphenyl)methoxy]carbonyl}phenyl)oxalate; bis(3,4,6-trichloro-2-{[(3-methylphenyl)methoxy]carbonyl}phenyl)oxalate; bis(3,4,6-trichloro-2-{[(4-methylphenyl)methoxy]carbonyl}phenyl)oxalate; bis(3,4,6-trichloro-2-{[(2,3-dimethylphenyl)methoxy]carbonyl}phenyl)oxalate; bis(3,4,6-trichloro-2-{[(2,4-dimethylphenyl)methoxy]carbonyl}phenyl)oxalate; bis(3,4,6-trichloro-2-{[3,4-dimethylphenyl)methoxy]carbonyl}phenyl)oxalate; bis(3,4,6-trichloro-2-{[(3,5-dimethylphenyl)methoxy]carbonyl}phenyl)oxalate; bis(3,4,6-trichloro-2-{[(2,6-dimethylphenyl)methoxy]carbonyl}phenyl)oxalate; bis(3,4,6-trichloro-2-{[(2-ethylphenyl)methoxy]carbonyl}phenyl)oxalate; bis(3,4,6-trichloro-2-{[(3-ethylphenyl)methoxy]carbonyl}phenyl)oxalate; bis(3,4,6-trichloro-2-{[(4-ethylphenyl)methoxy]carbonyl}phenyl)oxalate; bis(3,4,6-trichloro-2-{[2-(2-methylphenyl)ethoxy]carbonyl}phenyl)oxalate; bis(3,4,6-trichloro-2-{[2-(3-methylphenyl)ethoxy]carbonyl}phenyl)oxalate; bis(3,4,6-trichloro-2-{[2-(4-methylphenyl)ethoxy]carbonyl}phenyl)oxalate; bis{3,4,6-trichloro-2-[(2-phenylpropoxy)carbonyl]phenyl}oxalate; bis{3,4,6-trichloro-2-[(3-phenylpropoxy)carbonyl]phenyl}oxalate; bis{3,4,6-trichloro-2-[1-naphthalenylmethoxy)carbonyl]phenyl}oxalate; bis{3,4,6-trichloro-2-[2-naphthalenylmethoxy)carbonyl]phenyl}oxalate; bis{3,4,6-trichloro-2-[(2,2-diphenylethoxy)carbonyl]phenyl}oxalate; bis{3,4,6-trichloro-2-[(9-fluorenylmethoxy)carbonyl]phenyl}oxalate; and/or bis{3,4,6-trichloro-2-[(9-anthracenylmethoxy)carbonyl]phenyl}oxalate.

Additional examples of oxalate esters represented by general formula (I) are disclosed in U.S. Published Application No. 2011-0084243, the disclosure of such oxalate esters being incorporated herein by reference.

In some embodiments, the at least one oxalate ester is present in an amount ranging from 3 percent to 60 percent by weight, based upon the total weight of the oxalate system. In some embodiments, the at least one oxalate ester is present in an amount ranging from 8 percent to 50 percent by weight, based upon the total weight of the oxalate system. In some embodiments, the at least one oxalate ester is present in an amount ranging from 15 percent to 60 percent by weight, based upon the total weight of the oxalate system. In some embodiments, the at least one oxalate ester is present in an amount ranging from 10 percent to 40 percent by weight, based upon the total weight of the oxalate system. In some embodiments, the at least one oxalate ester is present in an amount ranging from 3 percent to 30 percent by weight, based upon the total weight of the oxalate system. In some embodiments, the at least one oxalate ester is present in an amount ranging from 5 percent to 30 percent by weight, based upon the total weight of the oxalate system.

In some embodiments, the at least one oxalate ester is present in an amount ranging from 20 percent to 60 percent by weight, based upon the total weight of the oxalate system. In some embodiments, the at least one oxalate ester is present in an amount ranging from 40 percent to 60 percent by weight, based upon the total weight of the oxalate system. In some embodiments, the at least one oxalate ester is present in an amount ranging from 3 percent to 20 percent by weight, based upon the total weight of the oxalate system.

In some embodiments, the at least one oxalate ester is present at 3 percent by weight, based upon the total weight of the oxalate system. In some embodiments, the at least one oxalate ester is present at 60 percent by weight, based upon the total weight of the oxalate system. In some embodiments, the at least one oxalate ester is present at more than 3 percent by weight, based upon the total weight of the oxalate system.

In some embodiments, the at least one oxalate ester is present at the weight percents and the weight percent ranges detailed above, based on the combined weight of the activator system and oxalate system.

In some embodiments, the at least one solvent may include, but is not limited to, alkyl benzoates, dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, acetyl trialkyl citrates, 2-acetyloxy isobutyrates, paraffinic liquids, isoparaffinic liquids, toluene, nitroethane, or a mixture of any of the above.

In some embodiments, the at least one first solvent is present in an amount ranging from 10 percent to 97 percent of the total weight of the oxalate system. In some embodiments, the at least one first solvent is present in an amount ranging from 20 percent to 80 percent of the total weight of the oxalate system. In some embodiments, the at least one first solvent is present in an amount ranging from 10 percent to 75 percent of the total weight of the oxalate system. In some embodiments, the at least one first solvent is present in an amount ranging from 30 percent to 80 percent of the total weight of the oxalate system. In some embodiments, the at least one first solvent is present in an amount ranging from 15 percent to 50 percent of the total weight of the oxalate system. In some embodiments, the at least one first solvent is present in an amount ranging from 50 percent to 97 percent of the total weight of the oxalate system. In some embodiments, the at least one first solvent is present in an amount ranging from 70 percent to 97 percent of the total weight of the oxalate system.

In some embodiments, the at least one first solvent is present at 10 percent of the total weight of the oxalate system. In some embodiments, the at least one first solvent is present at 40 percent of the total weight of the oxalate system. In some embodiments, the at least one first solvent is present at 60 percent of the total weight of the oxalate system. In some embodiments, the at least one first solvent is present at 75 percent of the total weight of the oxalate system. In some embodiments, the at least one first solvent is present at 97 percent of the total weight of the oxalate system.

In some embodiments, the at least one second solvent is present in an amount ranging from 10 percent to 97 percent of the total weight of the oxalate system. In some embodiments, the at least one second solvent is present in an amount ranging from 20 percent to 80 percent of the total weight of the oxalate system. In some embodiments, the at least one second solvent is present in an amount ranging from 10 percent to 75 percent of the total weight of the oxalate system. In some embodiments, the at least one second solvent is present in an amount ranging from 30 percent to 80 percent of the total weight of the oxalate system. In some embodiments, the at least one second solvent is present in an amount ranging from 15 percent to 50 percent of the total weight of the oxalate system. In some embodiments, the at least one second solvent is present in an amount ranging from 50 percent to 97 percent of the total weight of the oxalate system. In some embodiments, the at least one second solvent is present in an amount ranging from 70 percent to 97 percent of the total weight of the oxalate system.

In some embodiments, the at least one second solvent is present at 10 percent of the total weight of the oxalate system. In some embodiments, the at least one second solvent is present at 40 percent of the total weight of the oxalate system. In some embodiments, the at least one second solvent is present at 60 percent of the total weight of the oxalate system. In some embodiments, the at least one second solvent is present at 75 percent of the total weight of the oxalate system. In some embodiments, the at least one second solvent is present at 97 percent of the total weight of the oxalate system.

In some embodiments, the wavelength of light emitted is dependent upon the desired application of the device and the fluorescer chosen, and may include wavelengths in both the visual and infrared spectrum. In some embodiments, multiple fluorescers may be combined to allow for the emission of light at multiple wavelengths.

In some embodiments, the at least one fluorescer useful in the present disclosure include 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene; 2-chloro-9,10-bis(4-methoxyphenyl)anthracene; 9,10-bis(phenylethynyl)anthracene; 1-chloro-9,10-bis(phenylethynyl)anthracene; 1,8-dichloro-9,10-bis(phenylethynyl)anthracene; 1,5-dichloro-9,10-bis(phenylethynyl)anthracene; 2,3-dichloro-9,10-bis(phenylethynyl)anthracene; 5,12-bis(phenylethynyl)tetracene; 9,10-diphenylanthracene; 1,6,7,12-tetraphenoxy-N,N'-bis(2,6-diisopropylphenyl)-3,4,9,10-perylenedicarboximide; 1,6,7,12-tetraphenoxy-N,N'-bis(2,5-di-t-butylphenyl)-3,4,9,10-perylenedicarboximide; 1,7-dichloro-6,12-diphenoxy-N,N'-bis(2,6-diisopropylphenyl)-3,4,9,10-perylenedicarboximide; 1,6,7,12-tetra(pbromophenoxy)-N,N'-bis(2,6-diisopropylphenyl)-3,4,9,10-perylene dicarboximide; 1,6,7,12-tetraphenoxy-N,N'-dineopentyl-3,4,9,10-perylenedicarboximide; 1,6,7,12-tetra(p-t-butylphenoxy)-N,N'-dineopentyl-3,4,9,10-perylenedicarboximide; 1,6,7,12-tetra(o-chlorophenoxy)-N,N'-bis(2,6-diisopropylphenyl)-3,4,9,10-perylene dicarboximide; 1,6,7,12-tetra(p-chlorophenoxy)-N,N'-bis(2,6-diisopropyl-phenyl)-3,4,9,10-perylene dicarboximide; 1,6,7,12-tetra(o-fluorophenoxy)-N,N'-bis(2,6-diisopropylphenyl)-3,4,9,10-perylene dicarboximide; 1,6,7,12-tetra(p-fluorophenoxy)-N,N'-bis(2,6-diisopropylphenyl)-3,4,9,10-perylenedicarboximide; 1,6,7,12-tetraphenoxy-N,N'-diethyl-3,4,9,10-perylene dicarboximide; 1,7-dibromo-6,12-diphenoxy)-N,N'-bis(2-isopropylphenyl)-3,4,9,10-perylene dicarboximide; 16,17-dihexyloxyviolanthrone; 1,4-dimethyl-9,10-bis(phenylethynyl)anthracene, and/or mixtures thereof.

In some embodiments, the at least one fluorescer is present in an amount ranging from 0.05 percent to 0.9 percent by weight, based on the total weight of the oxalate system. In some embodiments, the at least one fluorescer is present in an amount ranging from 0.1 percent to 0.8 percent by weight, based on the total weight of the oxalate system. In some embodiments, the at least one fluorescer is present in an amount ranging from 0.15 percent to 0.9 percent by weight, based on the total weight of the oxalate system. In some embodiments, the at least one fluorescer is present in an amount ranging from 0.05 percent to 0.5 percent by weight, based on the total weight of the oxalate system. In some embodiments, the at least one fluorescer is present in an amount ranging from 0.2 percent to 0.7 percent by weight, based on the total weight of the oxalate system. In some embodiments, the at least one fluorescer is present in an amount ranging from 0.05 percent to 0.1 percent by weight, based on the total weight of the oxalate system. In some embodiments, the at least one fluorescer is present in an amount ranging from 0.05 percent to 0.3 percent by weight, based on the total weight of the oxalate system.

In some embodiments, the at least one fluorescer is present at 0.05 percent by weight, based on the total weight of the oxalate system. In some embodiments, the at least one fluorescer is present at 0.2 percent by weight, based on the total weight of the oxalate system. In some embodiments, the at least one fluorescer is present at 0.5 percent by weight, based on the total weight of the oxalate system. In some embodiments, the at least one fluorescer is present at 0.9 percent by weight, based on the total weight of the oxalate system.

In some embodiments, the at least one fluorescer is present at the weight percents and the weight percent ranges detailed above, based on the combined weight of the activator system and oxalate system.

In some embodiments, the ratio of solvents may be derived from the viscosity of the oxalate system at various temperatures and may also depend, at least in part, on the final use.

In some embodiments, the at least one inorganic salt may include, but is not limited to, sodium thiosulphate, potassium thiosulphate, cobalt acetate, copper acetate, lead acetate, cupric chloride, ferric chloride, calcium iodide, potassium iodide, and/or silver nitrate.

In some embodiments, the at least one inorganic salt is present in an amount ranging from 0.1 percent to 30 percent by weight, based on the total weight of the oxalate system. In some embodiments, the at least one inorganic salt is present in an amount ranging from 0.5 percent to 25 percent by weight, based on the total weight of the oxalate system. In some embodiments, the at least one inorganic salt is present in an amount ranging from 5 percent to 20 percent by weight, based on the total weight of the oxalate system. In some embodiments, the at least one inorganic salt is present in an amount ranging from 10 percent to 15 percent by weight, based on the total weight of the oxalate system. In some embodiments, the at least one inorganic salt is present in an amount ranging from 1 percent to 20 percent by weight, based on the total weight of the oxalate system. In some embodiments, the at least one inorganic salt is present in an amount ranging from 0.1 percent to 10 percent by weight, based on the total weight of the oxalate system. In some embodiments, the at least one inorganic salt is present in an amount ranging from 0.1 percent to 5 percent by weight, based on the total weight of the oxalate system.

In some embodiments, the at least one inorganic salt is present at 0.1 percent by weight, based on the total weight of the oxalate system. In some embodiments, the at least one inorganic salt is present at 30 percent by weight, based on the total weight of the oxalate system. In some embodiments, the at least one inorganic salt is present at 20 percent by weight, based on the total weight of the oxalate system. In some embodiments, the at least one inorganic salt is present at 15 percent by weight, based on the total weight of the oxalate system. In some embodiments, the at least one inorganic salt is present at 1 percent by weight, based on the total weight of the oxalate system. In some embodiments, the at least one inorganic salt is present at 2 percent by weight, based on the total weight of the oxalate system. In some embodiments, the at least one inorganic salt is present at 5 percent by weight, based on the total weight of the oxalate system.

In some embodiments, the at least one inorganic salt is present at the weight percents and the weight percent ranges detailed above, based on the combined weight of the activator system and oxalate system.

Non-Limiting Example 1

The experiments in Table I indicate that the ratio of the solvents, in this case butyl benzoate and diethyl diethylmalonate, used may be adjusted based, at least in part, on the desired operating temperature. The viscosities were measured using a Brookfield viscometer and the temperature of the solution recorded digitally during the experiment.

TABLE I

[Viscosity of butyl benzoate (BB) and diethyl diethylmalonate (DEDEM) mixtures at different temperatures]

| % DEDEM by weight | Temp. (° C.) | Viscosity (cP)) |
|---|---|---|
| 0 | 20 | 20 |
| 0 | 2 | 27 |
| 0 | −37 | Solid |
| 10 | 20 | 21 |
| 10 | 2 | 28 |
| 10 | −37 | Solid |
| 20 | 20 | 21 |
| 20 | 2 | 28 |
| 20 | −37 | Solid |
| 30 | 20 | 21 |
| 30 | 2 | 28 |
| 30 | −44 | Solid |
| 40 | 20 | 21 |
| 40 | 2 | 28 |
| 40 | −44 | 178* |

*Super cooled. Solid began to form by the end of the experiment.

Non-Limiting Example 2

The experiments in Table II indicate that the ratio of the solvents, in this case butyl benzoate and bis(2-ethylhexyl) adipate, used may require adjustment based, at least in part, on the desired operating temperature. The viscosities were measured using a Brookfield viscometer and the temperature of the solution recorded digitally during the experiment.

TABLE II

[Viscosity of butyl benzoate (BB) and bis(2-ethylhexyl) adipate (EHA) mixtures at different temperatures]

| % EHA by weight | Temp. (° C.) | Viscosity (cP) |
|---|---|---|
| 0 | −40 | Solid |
| 40 | −50 | Solid |
| 50 | −50 | Solid |
| 60 | −31 | 208 |
| 60 | −64 | 121200 |
| 70 | −64 | 30100 |

Non-Limiting Example 3

Oxalate formula A was prepared by dissolving 23.5 g of bis(2,4,5-trichloro-6-carbopentoxyphenyl)oxalate (CPPO) and 0.31 g of rubrene in 38.1 g of butyl benzoate (BB) and 38.1 g of diethyl diethylmalonate at 70 deg C. with a constant stream of dry nitrogen bubbling through the solution. The activator solution was prepared by combining 23 g of triethyl citrate, 20 g of diethylene glycol diethyl ether, 6 g of 50% aqueous hydrogen peroxide, and 1 g of sodium salicylate. The tests were conducted measuring the light output with an ILT 1700 light meter. First, the solutions were brought to the desired temperature (room temperature and 60 deg C.). The reaction vessel was placed into the high speed mixer and 0.5 g of sodium thiosulfate was added, then 5 mL of oxalate formula A was added and the mixer was turned on. The temperature was measured digitally at this time. The mixture at the colder temperature had warmed to −51 deg C. As rapidly as possible, add 5 mL of the activator solution and record the light output. The results are shown in FIG. 1. These results demonstrate the production of useable levels of light rapidly at low temperatures. FIG. 1 represents the chemical light output of oxalate formula A at −51 degrees C.

Non-Limiting Example 4

Figure 2:
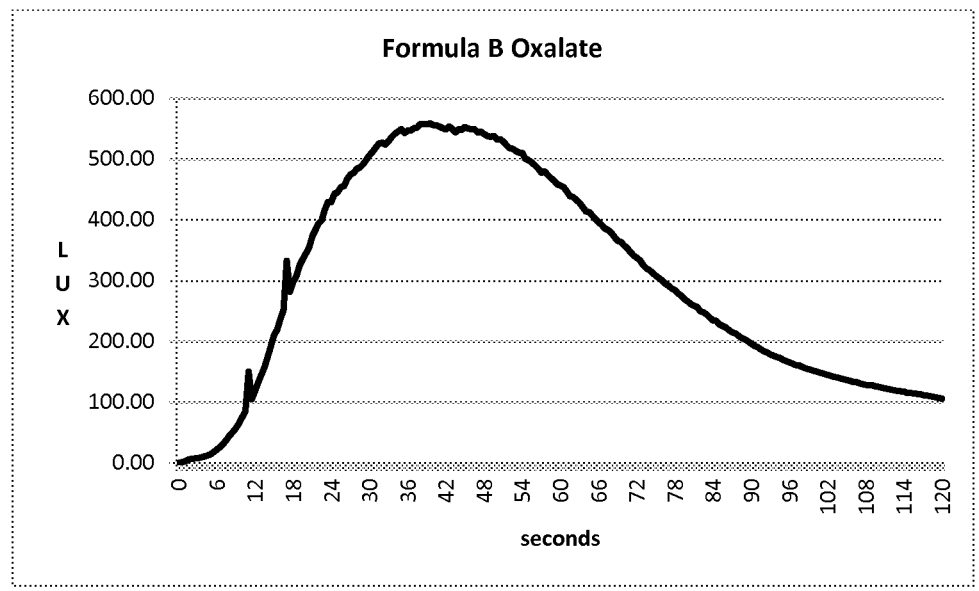
FIG. 2 illustrates aspects of some embodiments of the instant invention.

Oxalate formula B was prepared by dissolving 15 g of bis(2,4,5-trichloro-6-carbopentoxyphenyl)oxalate (CPPO) and 0.2 g of rubrene in 25.4 g of butyl benzoate (BB) and 59.4 g of bis(2-ethylhexyl) adipate (EHA) at 70° C. with a constant stream of dry nitrogen bubbling through the solution. The activator solution was prepared by combining 199.5 g of triethyl citrate, 250 g of diethylene glycol diethyl ether, 50 g of 50% aqueous hydrogen peroxide, and 0.5 g of sodium salicylate. The oxalate was sealed in glass ampoules under nitrogen so that each ampoule contained 0.8 g of oxalate solution and 0.15 g of sodium thiosulfate. The activator solution was sealed in glass ampoules so each ampoule contained 2.0 g of activator solution. The sealed ampoules were cooled to −86° C. in a freezer for a minimum of 2 hours. At that point they were placed in the in an ampoule crushing device with a light meter. The readings were started within one minute or less after removal from the freezer. The results are shown in FIG. 2. FIG. 2 represents the chemical light output of oxalate formula B at −86 degrees C.

In some embodiments, the instant invention provides a chemiluminescent system, including: an oxalate system, including: (a) at least one oxalate ester in an amount ranging from 3 to 60 percent by weight based on a total weight of the oxalate system, (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, and a combination thereof; where the at least one first solvent is present in an amount ranging from 10 to 97 percent by weight based on the total weight of the oxalate system, (c) at least one second solvent is selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, and a combination thereof; where the at least one second solvent is present in an amount ranging from 10 to 97 percent by weight based on the total weight of the oxalate system, (d) at least one fluorescer, and (e) at least one inorganic salt in an amount ranging from 0.1 to 30 percent by weight based on the total weight of the oxalate system, where a viscosity of the chemiluminescent system does not exceed 130,000 cP; and where a combination of the at least one first solvent and the at least one second solvent is present in a sufficient amount in the chemiluminescent system so as to result the chemiluminescent system, at a temperature ranging from −110 degrees Celsius to −10 degrees Celsius, producing a light having an illuminescence between 0.1 lx and 35,000 lx.

In some embodiments, the at least one oxalate ester is represented by formula (I):

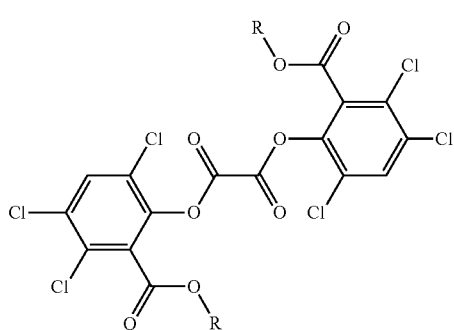

(I)

where R=$CH_2A$, and A is selected from the group consisting of an alkyl chain, alkyl ring, an aromatic ring, and a combination thereof, where R is linear or branched, and where R is from C4-15.

In some embodiments, the at least one oxalate ester is selected from the group consisting of: bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(3-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-trichloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,46-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)ethoxy]carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

In some embodiments, the at least one fluorescer is selected from the group consisting of: 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene, 2-chloro-9,10-bis(4-methoxyphenyl)anthracene, 9,10-bis(phenylethynyl)anthracene, 1-chloro-9,10-bis(phenylethynyl)anthracene, 1,8-dichloro-9,10-bis(phenylethynyl)anthracene, 1,5-dichloro-9,10-bis(phenylethynyl)anthracene, 2,3-dichloro-9,10-bis(phenylethynyl)anthracene, 5,12-bis(phenylethynyl)tetracene, 9,10-diphenylanthracene, 1,6,7,12-tetraphenoxy-N,N'-bis(2,6-diisopropylphenyl)-3,4,9,10-perylene dicarboximide, 1,6,7,12-tetraphenoxy-N,N' bis(2,5-di-t-butylphenyl)-3,4,9,10-perylene dicarboximide, 1,7-dichloro-6,12-diphenoxy-N,N'-bis(2,6-diisopropylphenyl)-

3,4,9,10-perylene dicarboximide, 1,6,7,12-tetra(p-bromophenoxy)-N,N'-bis(2,6-diisopropylphenyl)-3,4,9,10-perylene dicarboximide, 1,6,7,12-tetraphenoxy-N,N' dineopentyl-3,4,9,10-perylene dicarboximide, 1,6,7,12-tetra-(p-t-butylphenoxy)-N,N'-dineopentyl-3,4,9,10-perylenedicarboximide, 1,6,7,12-tetra(o-chlorophenoxy)-N,N'-bis(2,6-diisopropylphenyl)-3,4,9,10-perylene dicarboximide; 1,6,7,12-tetra(p-chlorophenoxy)-N,N'-bis(2,6-diisopropylphenyl)-3,4,9,10-perylene dicarboximide, 1,6,7,12-tetra(o-fluorophenoxy)-N,N'-bis(2,6-diisopropylphenyl)-3,4,9,10-perylene dicarboximide, 1,6,7,12-tetra(p-fluorophenoxy)-N,N'-bis(2,6-diisopropylphenyl)-3,4,9,10-perylenedicarboximide, 1,6,7,12-tetraphenoxy-N,N'-diethyl-3,4,9,10-perylene dicarboximide, 1,7-dibromo-6,12-diphenoxy-N,N'-bis(2-isopropylphenyl)-3,4,9,10-perylene dicarboximide, 16,17-dihexyloxyviolanthrone, and 1,4-dimethyl-9,10-bis(phenylethynyl)anthracene.

In some embodiments, the at least one inorganic salt is selected from the group consisting of: sodium thiosulphate, potassium thiosulphate, cobalt acetate, copper acetate, lead acetate, cupric chloride, ferric chloride, calcium iodide, potassium iodide, and silver nitrate.

In some embodiments, the at least one fluorescer is present in an amount ranging from 0.05 to 0.9 percent by weight based on the total weight of the oxalate system.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:
1. A chemiluminescent system, comprising:
   an oxalate system, comprising:
   (a) at least one oxalate ester in an amount ranging from 3 to 60 percent by weight based on a total weight of the oxalate system,
   (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, and a combination thereof;
      wherein the at least one first solvent is present in an amount ranging from 10 to 97 percent by weight based on the total weight of the oxalate system,
   (c) at least one second solvent is selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, and a combination thereof;
      wherein the at least one second solvent is present in an amount ranging from 10 to 97 percent by weight based on the total weight of the oxalate system,
   (d) at least one fluorescer, and
   (e) at least one inorganic salt in an amount ranging from 0.1 to 30 percent by weight based on the total weight of the oxalate system,
   wherein a viscosity of the chemiluminescent system does not exceed 130,000 cP; and
   wherein a combination of the at least one first solvent and the at least one second solvent is present in a sufficient amount in the chemiluminescent system so as to result the chemiluminescent system, at a temperature ranging from −110 degrees Celsius to −10 degrees Celsius, producing a light having an illuminescence between 0.1 lx and 35,000 lx.

2. The chemiluminescent system of claim 1, wherein the at least one oxalate ester is represented by formula (I):

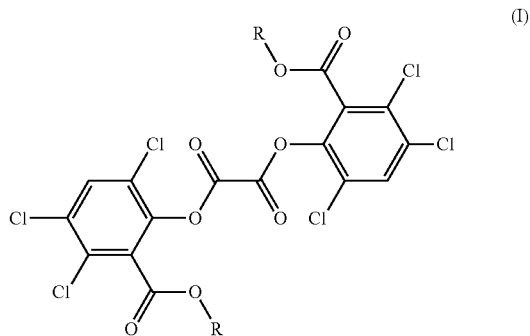

wherein R=$CH_2A$, and A is selected from the group consisting of an alkyl chain, alkyl ring, an aromatic ring, and a combination thereof,
wherein R is linear or branched, and
wherein R is from $C_{4-15}$.

3. The chemiluminescent system of claim 1, wherein the at least one oxalate ester is selected from the group consisting of: bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(3-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-trichloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,46-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2- methylphenyl)ethoxy]carbonyl}phenyl)oxalate, bis(3,4,6-trichloro-2-{[2-(3-methylphenyl)ethoxy]carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

4. The chemiluminescent system of claim 1, wherein the at least one fluorescer is selected from the group consisting of: 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene, 2-chloro-9,10-bis(4-methoxyphenyl)anthracene, 9,10-bis(phenylethynyl)anthracene, 1-chloro-9,10-bis(phenylethynyl)anthracene, 1,8-dichloro-9,10-bis(phenylethynyl)anthracene, 1,5-dichloro-9,10-bis(phenylethynyl)anthracene, 2,3-dichloro-9,10-bis(phenylethynyl)anthracene, 5,12-bis(phenylethynyl)tetracene, 9,10-diphenylanthracene, 1,6,7,12-tetraphenoxy-N,N'-bis(2,6-diisopropylphenyl)-3,4,9,10-perylene dicarboximide, 1,6,7,12-tetraphenoxy-N,N' bis(2,5-di-t-butylphenyl)-3,4,9,10-perylene dicarboximide, 1,7-dichloro-6,12-diphenoxy-N,N'-bis(2,6-diisopropylphenyl)-3,4,9,10-perylene dicarboximide, 1,6,7,12-tetra(p-bromophenoxy)-N,N'-bis(2,6-diisopropylphenyl)-3,4,9,10-perylene dicarboximide, 1,6,7,12-tetraphenoxy-N,N'dineopentyl-3,4,9,10-perylene dicarboximide, 1,6,7,12-tetra-(p-t-butylphenoxy)-N,N'-dineopentyl-3,4,9,10-perylenedicarboximide, 1,6,7,12-tetra(o-chlorophenoxy)-N,N'-bis(2,6-diisopropylphenyl)-3,4,9,10-perylene dicarboximide; 1,6,7,12-tetra(p-chlorophenoxy)-N,N'-bis(2,6-diisopropylphenyl)-3,4,9,10-perylene dicarboximide, 1,6,7,12-tetra(o-fluorophenoxy)-N,N'-bis(2,6-diisopropylphenyl)-3,4,9,10-perylene dicarboximide, 1,6,7,12-tetra(p-fluorophenoxy)-N,N'-bis(2,6-diisopropylphenyl)-3,4,9,10-perylenedicarboximide, 1,6,7,12-tetraphenoxy-N,N'-diethyl-3,4,9,10-perylene dicarboximide, 1,7-dibromo-6,12-diphenoxy-N,N'-bis(2-isopropylphenyl)-3,4,9,10-perylene dicarboximide, 16,17-dihexyloxyviolanthrone, and 1,4-dimethyl-9,10-bis(phenylethynyl)anthracene.

5. The chemiluminescent system of claim 1, the at least one inorganic salt is selected from the group consisting of: sodium thiosulphate, potassium thiosulphate, cobalt acetate, copper acetate, lead acetate, cupric chloride, ferric chloride, calcium iodide, potassium iodide, and silver nitrate.

6. The chemiluminescent system of claim 1, wherein the at least one fluorescer is present in an amount ranging from 0.05 to 0.9 percent by weight based on the total weight of the oxalate system.

* * * * *